Figure 2A:
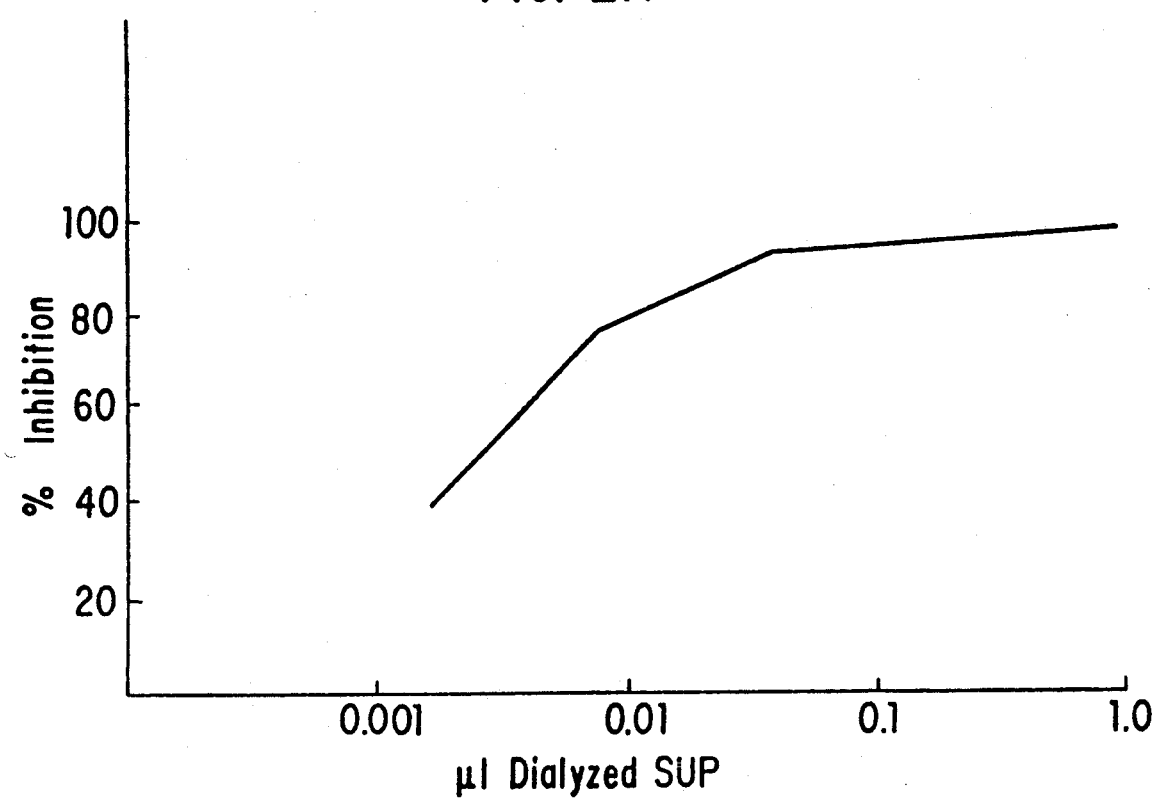

United States Patent [19]

Purchio et al.

[11] Patent Number: 5,244,793
[45] Date of Patent: Sep. 14, 1993

[54] TGF-β1/β2: A NOVEL CHIMERIC TRANSFORMING GROWTH FACTOR-BETA

[75] Inventors: Anthony F. Purchio; Linda Madisen, both of Seattle, Wash.

[73] Assignee: Oncogen, Seattle, Wash.

[21] Appl. No.: 667,246

[22] Filed: Mar. 8, 1991

Related U.S. Application Data

[63] Continuation of Ser. No. 284,972, Dec. 15, 1988, abandoned.

[51] Int. Cl.⁵ .................. C12P 21/00; C12N 5/00; C07H 21/00; C07K 13/00
[52] U.S. Cl. .................. 435/69.4; 435/69.7; 435/172.3; 435/240.2; 435/320.1; 536/23.51; 530/399; 935/13; 935/47
[58] Field of Search ............ 435/69.1, 69.7, 69.4, 435/172.3, 240.2, 320.1, 317.1; 536/27; 530/350, 399; 935/47, 13

[56] References Cited

PUBLICATIONS

Gentry et al., Mol. Cell. Biol. 7: 3418–3427 (1987).
Madisen et al., DNA 7: 1–8 (1988).
Meister et al., J. Gen. Virol. 67: 1633–1643 (1986).

Primary Examiner—Jasemine C. Chambers
Attorney, Agent, or Firm—Pennie & Edmonds

[57] ABSTRACT

A chimeric transforming growth factor-beta termed TGF-β1/β2, a DNA molecule encoding TGF-β1/β2, a mammaliam cell transformed with said DNA molecule, and a method for producing chimeric TGF-β1/β2 are disclosed.

21 Claims, 6 Drawing Sheets

FIG. 1A

```
                                                                              90                                    100
SIMIAN  Tyr Asn Ser Thr Arg Asp Arg Val Ala Gly Glu Ser Ala Glu Pro Glu Pro Glu
        TAC AAC AGC ACC CGC GAC CGG GTG GCC GGG GAG AGT GCG GAG CCG GAG CCG GAG :    300
HUMAN   ... ... ... ... ... ... ... ... ... ... ... ... ..A ... ..A ... ..T ... :

110                                    120
SIMIAN  Ala Asp Tyr Tyr Ala Lys Glu Val Thr Arg Val Leu Met Val Glu Thr His Asn Glu Ile
        GCC GAC TAC TAC GCC AAG GAG GTC ACC CGC GTG CTA ATG GTG GAA ACC CAC AAC GAA ATC :    360
HUMAN   ... ... ... ... ... ... ... ... ... ... ... ... ... ... ... ... ... ... ... ... :

130                                    140
SIMIAN  Tyr Asp Lys Phe Lys Gln Ser Thr His Ser Ile Tyr Met Phe Phe Asn Thr Ser Glu Leu
        TAT GAC AAG TTC AAG CAG AGC ACA CAC AGC ATA TAT ATG TTC TTC AAC ACA TCA GAG CTC :    420
HUMAN   ... ... ... ... ... ... ... ... ..T ... ... ... ... ... ... ... ... ... ... ... :

150                                                 Arg
SIMIAN  Arg Glu Ala Val Pro Glu Pro Val Leu Leu Ser Arg Ala Glu Leu Arg Leu Leu --- Arg
        CGA GAA GCA GTA CCT GAA CCT GTG TTG CTC TCC CGG GCA GAG CTG CGT CTG CTG --- AGG :    477
HUMAN   ... ... ... ... ..G ... ..C ... ... ... ... ... ... ... ... ... ... CTG AGG ... :

160                                  170
SIMIAN  Leu Lys Leu Lys Val Glu Gln His Val Glu Leu Tyr Gln Lys Tyr Ser Asn Asn Ser Trp
        CTC AAG TTA AAA GTG GAG CAG CAT GTG GAG CTG TAC CAG AAA TAC AGC AAC AAT TCC TGG :    537
HUMAN   ... ... ... ... ... ... ... ..C ... ... ... ... ... ... ... ... ... ... ... ... :

180                              190 Asp
SIMIAN  Arg Tyr Leu Ser Asn Arg Leu Leu Ala Pro Ser Asn Ser Pro Glu Trp Leu Ser Phe Asp
        CGA TAC CTC AGC AAC CGG CTG CTG GCG CCC AGC AAC TCG CCG GAG TGG TTG TCT TTT GAT :    597
HUMAN   ... ... ... ... ... ... ... ..A ... ... ... ... ... ..A ... ... ... ... ... ... :
```

FIG.1B

```
         200
SIMIAN   Val Thr Gly Val Val Arg Gln Trp Leu Ser Arg Gly Gly Glu Ile Glu Gly Phe Arg Leu   657
         GTC ACC GGA GTT GTG CGG CAG TGG TTG AGC CGC GGA GGG GAA ATT GAG GGC TTT CGC CTT
HUMAN    ... ... ... ... ... ... ... ... ... ... ... ... ... ... ... ... ... ... ... ...

220                                    230
SIMIAN   Ser Ala His Cys Ser Cys Asp Ser Lys Asp Asn Thr Leu Gln Val Asp Ile Asn Gly Phe    717
         AGC GCC CAC TGC TCC TGT GAC AGC AAA GAT AAC ACA CTG CAA GTG GAC ATC AAC GGG TTC
                                        Arg
HUMAN    ... ... ... ... ... ... ... ... ..G G.. ... ... ... ... ... ... ... ... ... ...

240                                          250
SIMIAN   Thr Thr Gly Arg Arg Gly Asp Leu Ala Thr Ile His Gly Met Asn Arg Pro Phe Leu Leu    777
         ACT ACC GGC CGC CGA GGT GAC CTG GCC ACA ATT CAT GGC ATG AAC CGG CCT TTC CTG CTT
HUMAN    ... ... ... ... ... ... ... ... ... ... ..C ... ... ... ... ... ... ... ... ...

260                                          270
SIMIAN   Leu Met Ala Thr Pro Leu Glu Arg Ala Gln His Leu Gln Ser Ser Arg His Arg Arg Ala    837
         CTC ATG GCC ACC CCA CTG GAG AGG GCC CAA CAT CTG CAA AGC TCC CGG CAC CGC CGA GCC
HUMAN    ... ... ... ... ... ..G ... ... ... ..G ... ... ... ... ... ... ... ... ... ...

280                                          290
SIMIAN   Leu Asp Thr Asn Tyr Cys Phe Arg Asn Val Gln Asp Asn Cys Cys Leu Arg Pro Leu Tyr    897
         CTG GAC ACC AAC TAC TGC TTC AGA AAT GTG CAG GAT AAT TGC TGC CTA CGT CCG CTT TAC
HUMAN    ... ... ... ... ..T ... ... ... ... ... ... ... ... ... ... ... ... ... ... ..C 300                                          310
SIMIAN   Ile Asp Phe Lys Arg Asp Leu Gly Trp Lys Trp Ile His Glu Pro Lys Gly Tyr His Ala    957
         ATT GAC TTC AAG AGG GAC CTC GGC TGG AAG TGG ATC CAC GAG CCC AAG GGC TAC CAT GCC
HUMAN    ..T ... ... ... ... ... ..T ..A ..G ... ... ... ... ... ... ... ... ... ... ...
```

FIG.1C

```
                      320                                                                                    330
SIMIAN       Asn Phe Cys Leu Gly Pro Cys Pro Tyr Ile Trp Ser Leu Asp Thr Gln Tyr Ser Lys Val
HUMAN        AAC TTC TGC CTG GGG CCC TGT CCC TAC ATT TGG AGC CTG GAC ACG CAG TAC AGC AAG GTC   1017
             ... ... ... ... ... ... ..C ... ... ... ... ... ... ... ... ... ... ... ... ...

340                                                                                    350
SIMIAN       Leu Ala Leu Tyr Asn Gln His Asn Pro Gly Ala Ser Ala Ala Pro Cys Cys Val Pro Gln
HUMAN        CTG GCC CTG TAC AAC CAG CAT AAC CCG GGC GCC TCG GCG GCC CCG TGC TGC GTG CCG CAG   1077
             ... ... ... ... ... ... ... ... ... ... ... ... ... ... ... ... ... ... ... ...

360                                                                                    370
SIMIAN       Ala Leu Glu Pro Leu Pro Ile Val Tyr Tyr Val Gly Arg Lys Pro Lys Val Glu Gln Leu
HUMAN        GCG CTG GAG CCA CTG CCC ATC GTG TAC TAC GTG GGC CGC AAG CCC AAG GTG GAG CAG CTG   1137
             ... ... ... ..G ... ... ... ... ... ... ... ... ... ... ... ... ... ... ... ...

380                                                                                    390
SIMIAN       Ser Asn Met Ile Val Arg Ser Cys Lys Cys Ser
HUMAN        TCC AAC ATG ATC GTG CGC TCC TGC AAA TGC AGC   TGA  GGCCCCGCCCCGCCCCACCCCGGCAG     1204
             ... ... ... ... ... ... ..G ... ... ... ...        ................T.........

SIMIAN       GCCCGGCGGCCCGCCCCACCCCGCTGTCTTGCCCTTGGGGGCTGTATTTAAGGACACCCGTGCCCCAAGCCCACC         1283
HUMAN        ........A...G.......G........C........A.................................

SIMIAN       TGGGGCCCCATTAAAGA                                                                 1300
HUMAN

TGF-β1/β2: A NOVEL CHIMERIC TRANSFORMING GROWTH FACTOR-BETA

This is a continuation of application Ser. No. 07/284,972, filed Dec. 15, 1988, now abandoned.

1. INTRODUCTION

The present invention relates to a novel chimeric transforming growth factor-beta termed TGF-β1/β2, to nucleotide sequences and expression vectors encoding TGF-β1/β2, and to methods for the production of TGF-β1/β2. The invention is exemplified by the production and secretion of TGF-β1/β2 by CHO cells transfected with expression vectors encoding a chimeric TGF-β1/β2 precursor gene. The chimeric gene product possesses TGF-β biological activity.

2. BACKGROUND OF THE INVENTION

Transforming growth factor-Beta (TGF-β) is a member of a recently described family of polypeptides that regulate cellular differentiation and proliferation. Other members of this family include Mullerian inhibitory substance (Cate et al., 1986, Cell 45:685-698), the inhibins (Mason et al., 1985, Nature 318:659-663) and a protein predicted from a transcript of the decapentaplegic gene complex of Drosophila (Padgett et al., 1987, Nature 325:81-84).

Four types of TGF-β have been identified and designated TGF-β1, TGF-β2, TGF-β1.2, and TGF-β3. The first described type, TGF-β1, consists of two identical disulfide linked subunits having molecular weights of 13,000 (Assoian et al., 1983, J. Biol. Chem. 258:7155-7160; Frolik et al, 1983, Proc. Natl. Acad. Sci. USA 80:3676-3680; Frolik et al., 1984, J. Biol. Chem. 260:10995-11000). It has been purified from several tissue sources including placenta (Frolik et al., 1983, Nature 325:81-84), blood platelets (Childs et al., 1982, Proc. Natl. Acad. Sci. USA 79:5312-5316; Assoian et al., 1983, J. Biol. Chem. 258:7155-7160) kidney (Roberts et al., 1983, Biochemistry 22:5692-5698), and demineralized bone (Seyedin et al., 1985, Proc. Natl. Acad. Sci. USA 82:119-123). cDNA clones coding for human (Derynck et al., 1985, Nature 316:701-705), mouse (Derynck et al., 1986, J. Biol. Chem. 261:4377-4379) and simian (Sharples et al., 1987, DNA 6:239-244) TGF-β1 have been isolated. DNA sequence analysis of these clones indicates that TGF-β1 is synthesized as a large precursor polypeptide, the carboxy terminus of which is cleaved to yield the mature TGF-β monomer. Strong sequence homology has been found throughout the TGF-β1 precursor protein from all of the above sources.

In the presence of 10% serum and epidermal growth factor, TGF-β1 promotes the anchorage independent growth of normal rat kidney fibroblasts (Roberts et al., 1981, Proc. Natl Acad. Sci. USA 78:5339-5343; Roberts et al., 1982, Nature 295:417-419; Twardzik et al., 1985, J. Cell. Biochem. 28:289-297); in the presence of 10% serum alone, it is able to induce colony formation of AKR-2B fibroblasts (Tucker et al., 1983, Cancer Res. 43:1518-1586). TGF-β1 has also been shown to cause fetal rat muscle mesenchymal cells to differentiate and produce cartilage specific macromolecules (Seyedin et al., 1986, J. Biol. Chem. 261:5693-5695).

In contrast to its effect on cell proliferation, TGF-β1 purified from human platelets has been shown to inhibit the growth of certain cells in culture (Tucker et al., 1984, Science 226:705-707). TGF-β1 has also been shown to inhibit the growth of several human cancer cell lines (Roberts et al., 1985, Proc. Natl. Acad. Sci. USA 82:119-123). This inhibitory/stimulatory effect of TGF-β1 may depend on several factors including cell type and the physiological state of the cells (for review see Sporn et al., 1986, Science 233:532-534).

TGF-β2, like TGF-β1, is a polypeptide of molecular weight 26,000 composed of two identical 13,000-dalton subunits which are disulfide linked (Chiefetz et al., 1987, Cell 48:409-415; Ikeda et al., 1987, Biochemistry 26:2406-2410) and has been isolated from bovine demineralized bone (Seydin et al., 1987, J. Biol. Chem. 262:1946-1949), porcine platelets (Cheifetz et al., 1987, 48:409-415), a human prostatic adenocarcinoma cell line, PC-3 (Ikeda et al., 1987, Biochemistry 26:2406-2410), and a human glioblastoma cell line (Wrann et al., 1987, EMBO 6:1633-1636). cDNA clones coding for human and simian TGF-β2 have been isolated (Madisen et al., 1988, DNA 7:1-8; Webb et al., 1988, DNA 7:493-497). The mature TGF-β2 monomer is cleaved from one of two larger precursor polypeptides, the mRNAs of which may arise via differential splicing (Webb et al., 1988, DNA 7:493-497).

TGF-β1 and TGF-β2 share 71% amino acid sequence identity in their mature regions, and 41% identity in their precursor structures. TGF-β3, the amino acid sequence of which has very recently been deduced from cDNA clones, appears to contain a C-terminal 112 amino acid sequence with about 80% homology to the mature monomers of TGF-β1 and TGF-β2 (Dijke et al, 1988, Proc. Natl. Acad, Sci. USA 85:4715-4719). TGF-β1.2 is a heterodimeric form comprising a β1 and β2 subunit linked by disulfide bonds (Cheifetz et al., 1987, Cell 48:409-415).

2.1. Intracellular Processing of TGF-β1

The amino portion of the precursor region of TGF-β1 from human, rodent and simian sources show a high degree of homology (Derynck et al., 1985 Nature 316:701-705; Derynck et al., 1986, J. Biol. Chem. 261:4377-4379; Sharples et al., 1987, DNA 6:239-244), suggesting an important biological function may be associated with this part of the molecule. Recent studies demonstrating that this portion of the TGF-β1 precursor is glycosylated and phosphorylated support this contention since one might assume that a cell would not go through the expense of performing these secondary modifications were it not for a specific function (Brunner at al., 1988, Mol. Cell. Biol. 8:2229-2232). These modifications may be important for dimerization of the precursor or for directing its movement out of the cell. There is evidence which suggests that glycosylation of the precursor is involved in the transport of mature TGF-β1 out of the cell (Purchio et al., 1988, J. Biol. Chem. 263:14211-14215).

The existence of what may either be intermediate precursor complexes involved in processing or expression artifacts in CHO cells expressing the simian TGF-β1 gene has been reported (Gentry et al., 1988, Mol. Cell. Biol. 8:4162-4168 press; Gentry et al., 1987, Mol. Cell. Biol. 7:3418-3427). These studies revealed that the TGF-β1 precursor synthesized by transfected CHO cells consists of pro-TGF-β1, mature TGF-β1, and the pro region of the precursor interlinked by disulfide bonds. Such disulfide-linked precursor complexes have also been observed in isolated latent forms of TGF-β1 (Miyazano et al., 1988, J. Cell. Biochem. Suppl.

12(A):200; Wakefield et al., 1987, J. Biol. Chem. Suppl. 11(A):46).

Gentry et al. (Gentry et al., 1988, Mol. Cell. Biol., 8:4162-4168) have proposed the following scheme for the processing of pre-pro-TGF-$\beta$1 in transfected CHO cells. (The amino acid position numbers referred to are from the published sequence of simian TGF-$\beta$1 (Sharples et al., 1987, DNA 6:239-244)). According to this proposed scheme, the first step involves signal peptide cleavage at the Gly-29/Leu-30 peptide bond. This cleavage event most likely occurs co-translationally during transit of the precursor through the rough endoplasmic reticulum membrane (Blobel and Dobberstein, 1975, J. Cell. Biol. 67:835-851; Walter et al., 1984, Cell 38:5-8). Following cleavage of the signal peptide, core glycosylation units (Rothman et al., 1978, Cell 15:1447-1454) are added to pro-TGF-$\beta$1 at each of three predicted N-glycosylation sites located at Asn-82, Asn-136 and Asn-176. The core glycosylated pro-TGF-$\beta$1 is then sequentially processed during transit through the Golgi to yield a phosphorylated glycoprotein containing complex, sialated oligosaccharides. At some stage during synthesis or transit, proteolytic cleavage at the dibasic residue and disulfide isomerization occurs, releasing mature TGF-$\beta$1.

In another recent study, mannose-6-phosphate was identified in the TGF-$\beta$1 precursor. Mannose-6-phosphate, a phosphorylated sugar analog, appears to play a fundamental role in the targeted transport and intercellular exchange of lysosomal enzymes (von Figura, 1986, Ann. Rev. Biochem. 55: 167-193). Specific receptors which recognize the mannose-6-phosphate residues of lysosomal enzymes have been identified and are essential components of the transport system. Secreted lysosomal proteins containing mannose-6-phosphate have been identified in the conditioned medium of tissue culture cells (Gal and Gottesman, 1986, J. Biol. Chem. 261:1760-1765; Capony et al., 1981, J. Cell. Biol. 104:253-262; Baumbach et al., 1984, Proc. Natl. Acad. Sci. USA 81:2985-2989; Sahagian and Gottesman, 1982, J. Biol. Chem. 257:11145-11150). It is possible that the mannose-6-phosphate residues of the TGF-$\beta$1 precursor may direct pro-TGF-$\beta$1 to lysosomes for proteolytic processing to yield mature TGF-$\beta$1. Alternatively, the mannose-6-phosphate residues may function to target the cleaved TGF-$\beta$1 precursor to lysosomes for degradation.

3. SUMMARY OF THE INVENTION

The present invention relates to the production of large quantities of a novel chimeric TGF-$\beta$, termed TGF-$\beta$1/$\beta$2, by eucaryotic host cells transfected with recombinant DNA vectors containing the TGF-$\beta$1/$\beta$2 precursor coding sequence controlled by expression regulatory elements. Simian TGF-$\beta$1 cDNA (Sharples et al., 1987, DNA 6:239-244) was modified so that the nucleotides encoding amino acid residue numbers 9-13, 17, 19, 25 and 26 of the mature TGF-$\beta$1 sequence were changed to the nucleotides encoding the corresponding amino acids of the mature TGF-$\beta$2 structure. Simian codon usage was maintained.

Expression vectors encoding the chimeric TGF-$\beta$1/$\beta$2 precursor under the regulatory control of Simian Virus 40 (SV 40) expression regulatory elements were constructed and used to transfect Chinese Hamster ovary (CHO) cells. CHO transfectants which synthesize and secrete high levels of mature TGF-$\beta$1/$\beta$2 were obtained. TGF-$\beta$1/$\beta$2 expression was amplified with methotrexate and amplified transfectants secreted as much as 1 mg/L mature TGF-$\beta$1/$\beta$2. Acidification of the conditioned media of the CHO transfectants resulted in maximal levels of bioactive TGF-$\beta$1/$\beta$2. It is believed that the high levels of mature TGF-$\beta$1/$\beta$2 secreted by the transfected CHO cells results from an unusual efficiency in the proteolytic processing of the chimeric precursor protein. Such increased processing efficiency may, in turn, result from structural characteristics affected by applicants' combination of the TGF-$\beta$1 and TGF-$\beta$2 amino acid sequences in the amino-terminal domain of the mature TGF-$\beta$ structure.

4. DESCRIPTION OF THE FIGURES

FIGS. 1A-1D. Nucleotide and deduced amino acid sequence of the TGF-$\beta$1/$\beta$2 hybrid protein encoded by expression plasmid p5$\beta$/dhfr.

Figure 2B:
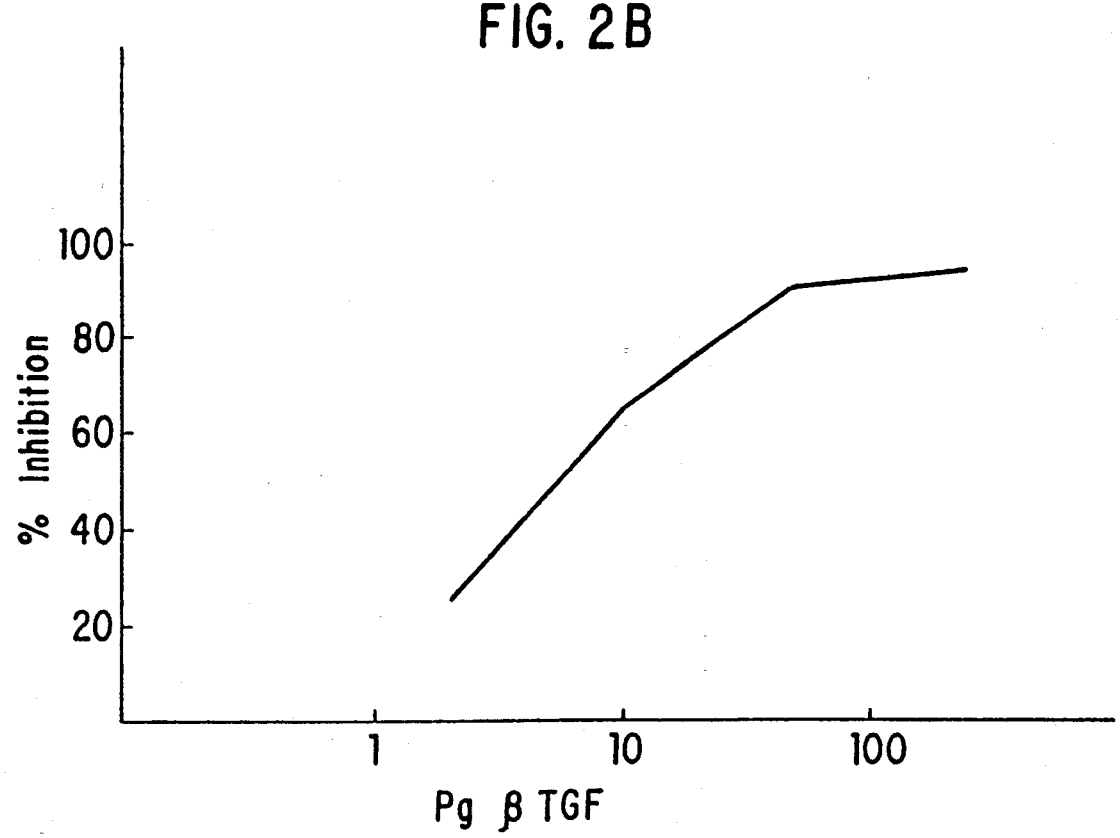

FIGS. 2A-2B. Bioactivity of conditioned media from 5$\beta$41,2.5 cells. Bioactivity was measured by the growth inhibition assay of CCL-64 mink lung epithelial cells. (A) Serum-free media conditioned by 5$\beta$41,2.5 cells for 24 hours was dialyzed against 0.2M acetic acid and assayed as described in Section 6.1.3., infra. (B) Standard growth inhibition curve for TGF-$\beta$1.

FIG. 3. Immunoblot analysis of proteins secreted by 5$\beta$41,2.5 cells. 5$\beta$41,2.5 cells were grown to confluence; media was dialyzed against 0.2M acetic acid and assayed by immunoblotting under nonreducing (lane 1) or reducing (lane 2) conditions with anti-TGF-$\beta$1$_{369-381}$ as described in Section 6.1.5., infra.

5. DESCRIPTION OF THE INVENTION

The present invention relates to TGF-$\beta$1/$\beta$2, to nucleotide sequences encoding TGF-$\beta$1/$\beta$2 and the TGF-$\beta$1/$\beta$2 precursor, and to the production of TGF-$\beta$1/$\beta$2 by recombinant DNA methods. TGF-$\beta$1/$\beta$2, a novel chimeric transforming growth factor-beta, is biologically active in the standard assay used to measure TGF-$\beta$1 bioactivity and is immunoreactive with TGF-$\beta$1-specific antibodies. A chimera structurally comprising a combination of TGF-$\beta$1 and TGF-$\beta$2 amino acid sequences, the TGF-$\beta$1/$\beta$2 of the invention is likely to carry a novel portfolio of biological activities, some of which may be similar or nearly identical to those exhibited by its parent molecules while others may be unique to TGF-$\beta$1/$\beta$2. With regard to those bioactivities which are similar or nearly identical to those of TGF-$\beta$1 or TGF-$\beta$2, this new factor may provide a more effective means of inducing corresponding biological responses and its use may therefore be a desirable alternative to TGF-$\beta$1 and TGF-$\beta$2 in various medical applications envisioned for the TGF-$\beta$s. Such applications include but are not limited to inducing or accelerating cell proliferation and differentiation and, inhibiting cell division. Thus TGF-$\beta$1/$\beta$2 may find uses in, for example, treating cancer and promoting wound healing.

The method of the invention may be divided into the following stages solely for the purposes of description: (a) generation of the coding sequence for the TGF-$\beta$1/$\beta$2 precursor; (b) construction of an expression vector which will direct the expression of the TGF-$\beta$1/$\beta$2 coding sequence; (c) transfection of appropriate host cells which are capable of replicating, expressing the gene and processing the gene product to produce the mature form of TGF-$\beta$1/$\beta$2 and/or TGF-$\beta$ 1/$\beta$2 precursors; and (d) identification and purification of the TGF-$\beta$1/$\beta$2 precursors and the mature, biologically active TGF-$\beta$1/$\beta$2.

Once a transfectant is identified that expresses high levels of TGF-β1/β2 precursors and/or mature TGF-β1/β2, the practice of the method of the invention involves the expansion of that clone and isolation of the gene product expressed.

The method of the invention is demonstrated herein, by way of examples in which simian TGF-β1 precursor cDNA (Sharples et al., 1987, DNA 6:239-244) is modified so that the nucleotides encoding amino acid residue numbers 9-13, 17, 19, 25 and 26 of the mature simian TGF-β1 sequence are changed to the nucleotides encoding the corresponding amino acids in the mature TGF-β2 structure, while maintaining simian codon usage. The resulting chimeric TGF-β1/β2 precursor coding sequence is then used to construct expression vectors which are capable of directing the synthesis of the mature TGF-β1/β2 product.

The various aspects of the method of the invention are described in more detail in the subsections below and in the examples that follow.

5.1. Generation of the Chimeric TGF-β1/β2 Coding Sequence

The nucleotide coding sequence for the chimeric TGF-β1/β2 is depicted in FIG. 1. In the practice of the method of the invention, this nucleotide sequence or its functional equivalent can be used to generate the recombinant molecules which will direct the expression of the TGF-β1/β2 product. Due to the degeneracy of the nucleotide coding sequences, other DNA sequences as depicted in FIG. 1 may be used in the practice of the present invention. Such alterations of the nucleotide sequence of FIG. 1 include deletions, additions or substitutions of different nucleotide residues resulting in a sequence that encodes the same or a functionally equivalent gene product. The gene product may contain deletions, additions or substitutions of amino acid residues within a sequence, which result in a silent change thus producing a bioactive product. Such amino acid substitutions may be made on the basis of similarity in polarity, charge, solubility, hydrophobicity, hydrophilicity and/or the amphipathic nature of the residues involved. For example, negatively charged amino acids include aspartic acid and glutamic acid; positively charged amino acids include lysine and arginine; amino acids with uncharge dpolar head groups or nonpolar head groups having similar hydrophilicity values include the following: leucine, isoleucine, valine; glycine, alanine; asparagine, glutamine; serine, threonine; phenylalanine, tyrosine.

The nucleotide sequence for simian TGF-β1 may be obtained from simian cell sources (Sharples et al., 1989, DNA 6:239-244). The nucleotide sequence of the chimeric TGF-β1/β2 in FIG. 1 may be prepared by methods known in the art including but not limited to the use of DNA restriction enzymes, synthetic oligonucleotides, and DNA ligases. Alternatively, the coding sequence of FIG. 1 may be synthesized in whole or in part using chemical methods well known in the art.

In a specific embodiment of the invention, the coding sequence for simian TGF-β1 was obtained from a full length cDNA clone obtained from an African green monkey cell line, BSC-40 (Sharples et al., 1987, supra). The coding sequence of chimeric TGF-β1/β2 depicted in FIG. 1 was then derived from the simian TGF-β1 cDNA by removing and replacing the coding sequences of amino acid residue numbers 9, 10, 11, 12, 13, 17, 19, 25 and 26 of the mature TGF-β1 molecule with the coding sequences for amino acid residue numbers 9, 10, 11, 12, 13, 17, 19, 25 and 26 of the mature TGF-β2 molecule (Madisen et al., 1988, DNA 7:1-8) using gene construction techniques.

5.2. Construction of Expression Vectors Containing the Chimeric TGF-β1/β2 Coding Sequence In order to express biologically active, mature TGF-β1/β2, an expression vector/host system should be chosen which provides not only for high levels of transcription and translation but for the correct processing of the gene product. This is especially important when employing the entire coding sequence of the chimeric TGF-β1/β2 precursor in the expression constructs because, like TGF-β1 and TGF-β2, the mature chimeric TGF-β1/β2 is believed to be released from a precursor molecule or complex of molecules via cellular processing events. In addition, an expression/host cell system which provides for secretin of the product may be desirable.

In particular, it appears that mature TGF-β1/β2 is a disulfide linked homodimer of 112 amino acids per subunit formed by cellular processing events believed to be similar to those which form mature TGF-β1 and TGF-β2. The TGF-β1/β2 precursor has three potentional N-glycosylation sites in its pro domain (Sharples et al., 1987, DNA 6:239-244). Studies involving TGF-β1 have determined that N-glycosylation and phosphorylation in the pro domain of TGF-β1 occurs in transfected CHO cells, implicating an important functional role for the precursor in the cellular systhesis and release or seretion of the mature molecule (Brunner et al., 1988, Mol. Cell. Biol. 8:2229-2232). The presence of mannose-6-phosphate in the TGF-β1 precursor also supports the hypothesis that the precursor has independent functional activity (Purchio et al., 1988, J. Biol. Chem. 263:14211-14215). Since the chimeric TGF-β1/β2 precursor contains the simian TGF-β1 pro domain, applicants believe it likely that the TGF-β1/β2 precursor is functionally active and important to the correct processing the mature TGF-β1/β2 molecule. Thus, the ability of a host cell used in the expression system to correctly express and process chimeric TGF-β1/β2 is important to the production of a mature, bioactive product.

In a specific embodiment described herein, mature bioactive TGF-β1/β2 is successfully produced using simian virus 40 (SV40) expression control elements in a Chinese Hamster Ovary (CHO) host cell system. However, a variety of other animal host/expression vector systems (i.e., vectors which contain the necessary elements for directing the replication, transcription and translation of the TGF-β1/β2 coding sequence in an appropriate host cell) may be utilized equally well by the skilled artisan. These include, but are not limited to, virus expression vector/mammalian host cell systems (e.g., cytomegalovirus, vaccinia virus, adenovirus, and the like); insect virus expression vector/insect cell systems (e.g., baculovirus); or nonviral promoter expression systems derived from the genomes of mammalian cells (e.g., the mouse metallothionein promoter).

The expression elements of these vectors vary in their strength and specificities. Depending on the host/vector system utilized, any one of a number of suitable transcription and translation elements may be used. For instance, when cloning in mammalian cell systems, promoters isolated from the genome of mammalian cells, (e.g. mouse metallothionein promoter) or from viruses that grow in these cells, (e.g. vaccinia virus 7.5K promoter) may be used. Promoters produced by recombinant DNA or synthetic techniques may also be used to provide for transcription of the inserted sequences.

Specific initiation signals are also required for sufficient translation of inserted protein coding sequences. These signals include the ATG initiation codon and adjacent sequences. For example, in cases where only a portion of the TGF-β1/β2 coding sequence is inserted, exogenous translational control signals, including the ATG initiation codon must be provided. Furthermore, the initiation codon must be in phase with the reading frame of the TGF-β1/β2 coding sequences to ensure translation of the entire insert. These exogenous translational control signals and initiation codons can be of a variety of origins, both natural and synthetic. The efficiency of expression may be enhanced by the inclusion of transcription attenuation sequences, enhancer elements, and the like.

Any of the methods previously described for the insertion of DNA fragments into a vector may be used to construct expression vectors containing the TGF-β1/β2 coding sequence and appropriate transcriptional/translational control signals. These methods may include in vitro recombinant DNA techniques, synthetic techniques and in vivo recombinations (genetic recombination).

In cases where an adenovirus is used as an expression vector, the TGF-β1/β2 coding sequence may be ligated to an adenovirus transcription/translation control complex, e.g., the late promoter and tripartite leader sequence. This chimeric gene may then be inserted in the adenovirus genome by in vitro or in vivo recombination. Insertion in a nonessential region of the viral genome (e.g., region E1 or E3) will result in a recombinant virus that is viable and capable of expressing chimeric TGF-β1/β2 in infected hosts. Similarly, the vaccinia 7.5K promoter may be used.

An alternative expression system which could be used to express TGF-β1/β2 is an insect system. In one such system, *Autographa californica* nuclear polyhedrosis virus (AcNPV) is used as a vector to express foreign genes. The virus grows in *Spodoptera frugiperda* cells. The TGF-β1/β2 coding sequence may be cloned into non-essential regions (for example, the polyhedrin gene) of the virus and placed under the control of an AcNPV promoter (for example, the polyhedrin promoter). Successful insertion of the TGF-β1/β2 coding sequence will result in inactivation of the polyhedrin gene and production of non-occluded recombinant virus (i.e., virus lacking the proteinaceous coat encoded by the polyhedrin gene). These recombinant viruses are then used to infect *Spodoptera frugiperda* cells in which the inserted gene is expressed.

In addition, a host cell strain may be chosen which modulates the expression of the inserted sequences, or modifies and processes the gene product in the specific fashion desired. Expression from certain promoters can be elevated in the presence of certain inducers, (e.g. zinc and cadmium ions for metallothionein promoters). Therefore, expression of the genetically engineered TGF-β1/β2 may be controlled. This is important if the protein product of the cloned foreign gene is lethal to host cells. Furthermore, post-translational modifications such as glycosylation, and processing events such as proteolytic cleavage of protein products, may be important to the functionality of the protein. Different host cells have characteristic and specific mechanisms for the post-translational processing and modification of proteins. Appropriate cell lines or host systems can be chosen to ensure the correct modification and processing of the foreign protein expressed.

In a specific embodiment of the invention, an expression vector containing the TGF-β1/β2 coding sequence in tandem with the mouse dihydrofolate reductase gene (dhfr) under the control of SV40 regulatory sequences is constructed and used to transfect dhfr-deficient CHO cells. CHO transfectants expressing the dhfr phenotype are isolated by propagation in selective media. To increase the level of expression of TGF-β1/β2, transfectants may be exposed to increasing concentrations of methotrexate in order to isolate clones transcribing amplified levels of TGF-β1/β2 mRNA. TGF-β1/β2 mRNA levels may be assayed at various stages of amplification by solution hybridization (Uhler et al., 1986, Proc. Natl. Acad. Sci. U.S.A. 83:1300–1304).

5.3. Identification of Transfectants Expressing Chimeric TGF-β1/β2

The host cells which contain the TGF-β1/β2 coding sequence and which express the biologically active, mature product may be identified by at least four general approaches: (a) DNA-DNA hybridization; (b) the presence or absence of "marker" gene functions; (c) assessing the level of transcription as measured by the expression of TGF-β1/β2 mRNA transcripts in the host cell; and (d) detection of the mature gene product as measured by immunoassay and, ultimately, by its biological activities.

In the first approach, the presence of the TGF-β1/β2 coding sequence inserted in the expression vector can be detected by DNA-DNA hybridization using probes comprising nucleotide sequences that are homologous to the TGF-β1/β2 coding sequence substantially as shown in FIG. 1, or portions or derivatives thereof.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if the TGF-β1/β2 coding sequence is inserted within a marker gene sequence of the vector, recombinants containing the TGF-β1/β2 coding sequence can be identified by the absence of the marker gene function. Alternatively, a marker gene can be placed in tandem with the TGF-β1/β2 sequence under the control of the same or different promoter used to control the expression of the TGF-β1/β2 coding sequence. Expression of the marker in response to induction or selection indicates expression of the TGF-β1/β2 coding sequence.

In the third approach, transcriptional activity for the TGF-β1/β2 coding region can be assessed by hybridization assays. For example, polyadenylated RNA can be isolated and analyzed by Northern blot using a probe homologous to the TGF-β1/β2 coding sequence or particular portions thereof. Alternatively, total nucleic acids of the host cell may be extracted and assayed for hybridization to such probes.

In the fourth approach, the expression of the mature protein product can be assessed immunologically, for example by Western blots, immunoassays such as immunoblotting, radioimmunoprecipitation, enzyme-linked immunoassays, and the like. The ultimate test of the success of the expression system, however, involves the detection of the biologically active TGF-β1/β2 gene product. Where the host cell secretes the gene product, the cell free media obtained from the cultured transfectant host cell may be assayed for TGF-β1/β2 activity. Where the gene product is not secreted, cell lysates may be assayed for such activity. In either case, biological assays such as the growth inhibition assay described herein or the like may be used.

Once a clone producing high levels of mature TGF-β1/β2 is identified, the clone may be expanded and the TGF-β1/β2 may be purified using techniques well known in the art. Such methods include immunoaffinity purification, chromatographic methods including high performance liquid chromatography, and the like.

6. EXAMPLE: PRODUCTION OF TGF-β1/β2 BY EXPRESSION IN CHINESE HAMSTER OVARY CELLS

A recombinant plasmid encoding TGF-β1 precursor in which amino acids 9, 10, 11, 12, 13, 17, 19, 25 and 26 of the mature TGF-β1 sequence were replaced by the corresponding amino acids of the mature TGF-β2 sequence was constructed. Specifically, amino acid 9 of mature TGF-β1 (serine) was replaced by arginine, amino acid number 10 (serine) was replaced by asparagine, amino acid number 11 (threonine) was replaced by valine, amino acid number 12 (glutamic acid) was replaced by glutamine, amino acid number 13 (lysine) was replaced by aspartic acid, amino acid number 17 (valine) was replaced by leucine, amino acid number 19 (glutamine) was replaced by proline, amino acid number 25 (arginine) was replaced by lysine and amino acid number 26 (lysine) was replaced by arginine. The construct was used to transfect CHO cells. Transfectants which produced and secreted a mature, bioactive, chimeric TGF-β1/β2 were isolated.

6.1. Materials and Methods

6.1.1. DNA TRANSFECTIONS

Approximately 24 hours after seeding $10^6$ dhfr-deficient CHO cells onto 100 mm dishes, the cultures were transfected with 1 μg of NdeI linearized p5β/dhfr plasmid and 19 μg of calf thymus DNA as carrier as a calcium phosphate precipitate (Wigler, M., et al., 1979, Proc. Natl. Acad. Sci. U.S.A. 76:1373-1376). Briefly, 20 ug of plasmid plus carrier DNA was added to 1 ml of 250 mM sterile CaCl$_2$. The DNA solution (1 ml) was added dropwise to a 1 ml portion of 2× HEPES solution (280 mM NaCl, 50 mM HEPES, 1.5 mM sodium phosphate, pH 7.1) while bubbling and the mixture was allowed to sit on ice for 30 minutes. The precipitate was then dispersed dropwise over the cells containing 10 ml of F12 media (Gibco). After incubation at 37° C. for 4 hours, the media was removed and replaced with 10 ml of F12 media containing 25% glycerol for 90 seconds at room temperature. Cells were rinsed once with 20 ml of F12 media and incubated in the nonselective F12 media (20 ml) for an additional 48 hours. Selection for dhfr expressing transfectants was accomplished by replacing the media with DMEM supplemented with 10% dialyzed FBS (Gibco) and 150 ug/ml L-proline. Colonies were observed after culturing the cells 10-14 days in the selection media.

6.1.2. SELECTION OF METHOTREXATE RESISTANT CELLS

Dihydrofolate reductase (dhfr) amplified cells were derived from the primary transfectants essentially as described (Gasser, C. S. and Schimke, R. T., 1986, J. Biol. Chem. 261:6938-6946). After expansion, $10^5$ cells were seeded onto 100 mm dishes and adapted to increasing concentrations of methotrexate (100 nM; 500 nM; 2,500 nM; 10,000 nM; 20,000 nM). The initial concentration of methotrexate was 100 nM. The plate containing visible colonies was trypsinized and adapted to that concentration of methotrexate for at least two additional 1:5 cell passages. Cells ($10^5$) were then seeded onto 100 mm dishes in the next highest concentration of methotrexate. The dish containing visible colonies was again trypsinized and adapted in the methotrexate containing medium. Cells were frozen back at various stages of amplification in media containing 40% FBS, 10% dimethyl sulfoxide and 50% DMEM. Methotrexate was not included in the freezing media.

6.1.3. GROWTH INHIBITION ASSAY

Mink lung epithelial cells, Mv 1 Lu (Accession Number CCL-64, American Type Culture Collection), which are extremely sensitive to TGF-β were utilized for the growth inhibition assay. The assay was performed using the thymidine analog 5'-[$^{125}$I]-iodo-2'deoxyuridine ($^{125}$IdU) to assess DNA synthesis. One unit of activity was defined as the amount required to inhibit 50% incorporation of $^{125}$IdU compared to untreated CCL-64 cells.

To assay transfected cells for secretion of active TGF-β1/β2, serum free supernatants were collected from one 24 hour collection on confluent cultures of cells and dialyzed extensively against 0.2M acetic acid. Samples were diluted into sterile complete culture medium for assays.

6.1.4. PEPTIDE SYNTHESIS AND PRODUCTION OF ANTIBODIES

Peptides were synthesized by solid phase techniques on a Beckman 990 instrument, and cleaved from the resin as previously described (Gentry, L. E., et al., 1983, J. Biol. Chem. 258:11219-11228; Gentry, L. E. and Lawton, A., 1986, Virology 152:421-431). Purification was accomplished by preparative high performance liquid chromatography. The composition of the peptides was confirmed by amino acid analysis.

Synthetic peptides were conjugated to bovine gamma-globulin through the cysteine residue. Coupling reactions were performed essentially as described (Gentry and Lawton, 1986, supra). The efficiencies of peptide conjugations ranged from 8 to 26 molecules of peptide covalently attached per molecule of gamma-globulin.

New Zealand white rabbits were primed at three to six sites by combined subcutaneous and intradermal inoculations with the peptide conjugates (100 ug equivalents of peptide) emulsified in Freunds complete adjuvant. Booster inoculations were administered at 2-3 week intervals. Bleedings were taken 7-14 days following the boosts.

Anti-peptide antibodies direced toward peptide sequences within the TGF-β1 molecule were generated in rabbits using synthetic peptides as immunogens (Gentry et al., 1987, Mol. Cell. Biol. 7:3418-3427). One of the antibodies (anti-TGF-β1$_{369-381}$) was directed toward epitopes present within the mature form of the TGF-β growth factor. The other two antibodies (anti-TGF-β1$_{81-94}$ and anti-TGF-β1$_{225-236}$) are precursor-specific and are directed toward peptide sequences present only within the precursor molecule of TGF-β1.

6.1.5. IMMUNOBLOTTING

Proteins were fractionated on 7.5%-17.5% gradient SDS-polyacrylamide gels and transferred to unmodified nitrocellulose (0.45 um; Schleicher and Schuell) for 1 hour at 24 volts at 4° C. (Burnette, W. N., 1981, Anal. Biochem. 112:195-203). Excess binding capacity of the nitrocellulose was blocked by incubation with 2.5% BLOTTO (Johnson, D. A., et al., 1984, Gene Anal. Techn. 1:3-8) in phosphate-buffered saline (PBS) containing 0.2% NP-40. Rabbit anti-serum diluted 1:75 in 2.5% BLOTTO was incubated with the blocked nitrocellulose sheets for 2 hours at room temperature. After washing away excess antibody by five 5-minute washes in 2.5% BLOTTO, the nitrocellulose sheets were incubated with alkaline phosphatase-conjugated Protein A diluted 1:500 in 2.5% BLOTTO. Following a two hour incubation, the nitrocellulose sheets were washed 5 times in PBS (5 minute washes) containing 0.2% NP-40 and developed (Leary et al., 1983, Proc. Natl. Acad. Sci. U.S.A. 80:4045-4049).

6.1.6. CONSTRUCTION OF PLASMID PROGRAMMING THE SYNTHESIS OF TGF-$\beta 1/\beta 2$ The plasmid programming the synthesis of the chimeric TGF-$\beta 1/\beta 2$ protein, p5$\beta$/dhfr, was constructed as follows. pAc$\beta$TGF-1, a baculovirus vector derived from pAc373 (Miyamoto et al., 1985, Mol. Cell. Biol. 5:2860-2865; Madisen et al., 1987, Virology 158:248-250), which contains the 1.4 Kb PstI-EcoRI coding sequence of TGF-$\beta 1$ (Sharples et al., 1987, DNA 6:239-244) cloned into the PstI-EcoRI site of pAc611 (Miyamoto et al., 1985, Mol. Cell. Biol. 5:2860-2865; Madisen et al., 1987, Virology 158:248-250), was digested with BamHI and EcoRI and the 375 bp fragment of the TGF-$\beta 1$ coding sequence was isolated (Fragment 1). pSV2-$\beta$TGF (Gentry et al., 1987, Mol. Cell. Biol. 7:3418-3427) was digested with ApaI and EcoRI and the 3.5 Kb fragment was isolated (Fragment 2).

Complementary synthetic oligonucleotides having the sequences shown below were synthesized on an Applied Biosystems Oligonucleotide Synthesizer and purified from an acrylamide gel. Phosphates were added with T4 kinase and equimolar amounts of the kinased oligonucleotides were annealed. The annealed double stranded synthetic DNA was then ligated to fragments '1' and '2' described above. The ligation mixture was used to transform E. coli and 5$\beta$pSV2(Hpa$^-$Eco$^+$) was isolated.

```
5' - CAA CAT CTG CAA AGC TCC CGG CAC CGC CGA GCC
    CTG GAC ACC AAC TAC TGC TTC AGA AAT GTG CAG
    GAT AAT TGC TGC CTA CGT CCG CTT TAC ATT GAT
    TTC AAG AGG GAT CTA GGG TGG AAA TG - 3'

5'  GAT CCA TTT CCA CCC TAG ATC CCT CTT GAA ATC
    AAT GTA AAG CGG ACG TAG GCA GCA ATT ATC CTG
    CAC ATT TCT GAA GCA GTA GTT GGT GTC CAG GGC
    TCG GCG GTG CCG GGA GCT TTG CAG ATG TTG GGC C - 3'
```

5$\beta$pSV2(Hpa$^-$Eco$^+$) was digested with EcoRI, filled in with Klenow enzyme, digested with HindIII and the 1.4 Kb fragment containing the chimeric TGF-$\beta 1/\beta 2$ coding sequence was isolated (Fragment 3). 5$\beta$pSV2 was constructed by ligating Fragment 3 into pSV2,neo which had previously been digested with HindIII and HpaI to eliminate the neo gene.

5$\beta$pSV2 was digested with EcoRI, filled in with Klenow enzyme, digested with NdeI and the 2.6 Kb NdeI-EcoRI (blunt) fragment was isolated and ligated to pSV2/dhfr (Gentry et al., 1987, Mol. Cell. Biol. 7:3718-3727) which had been digested with NdeI and PvuII. The ligation mixture was used to transform E. coli and p5$\beta$/dhfr was isolated. The nucleotide and deduced amino acid sequences of the chimeric TGF-$\beta 1/\beta 2$ molecule encoded by p5$\beta$/dhfr are shown in FIG. 1.

6.2. Expression of TGF-$\beta 1/\beta 2$ in CHO Cells p5$\beta$/dhfr was transfected into CHO cells and single clones were amplified with methotrexate as described in Section 6.1., supra. One such amplified clone, CHO-5$\beta$41,2.5, was chosen for further characterization.

CHO-5$\beta$41,2.5 cells were grown to confluence in 2.5 $\mu$M methotrexate. Media was replaced with serum free media and, after 24 hr, was collected and dialyzed for 48 hr against 0.2M acetic acid. Dialyzed, conditioned supernatants were assayed for bioactivity by inhibition of DNA synthesis of CCL-64 cells as described in Section, 6.1.3., supra. CHO-5$\beta$41,2.5 cells secrete approximately 2 mg/L of bioactive chimeric TGF-$\beta 1/\beta 2$ (FIG. 2).

TGF-$\beta$ related proteins secreted by these cells were analyzed by immunoblotting using anti-peptide antibodies directed against mature TGF-$\beta 1$ as described in Section 6.1.5., supra FIG. 3 shows that CHO-5$\beta$41,2.5 cells secrete immunoreactive proteins migrating at 90 to 100 kilodaltons and at 24 kilodaltons when analyzed on SDS-PAGE under nonreducing conditions (FIG. 3, lane 1). The 24 kilodalton band represents the mature TGF-$\beta 1/\beta 2$ dimer and the 90 to 100 kilodalton protein probably represents mature TGF-$\beta 1/\beta 2$ disulfide-bonded to precursor sequences (Gentry et al., 1987, Mol. Cell. Biol. 7:3418-3427).

Under reducing conditions (FIG. 3, lane 2), the majority of the proteins migrate at 12 kilodaltons, representing the mature TGF-$\beta 1/\beta 2$ monomer. Note the lack of immunoreactive material in the 45 to 55 kilodalton range observed in a similar analysis of recombinant proteins expressed in CHO cells tranfected with plasmids encoding the simian TGF-$\beta 1$ gene (Gentry et al., 1987, Mol. Cell. Biol. 7:3418-3427) suggesting that chimeric TGF-$\beta 1/\beta 2$ is proteolytically processed more efficiently than its parent molecule TGF-$\beta 1$. In addition, CHO-5$\beta$41,2.5 cells secrete about 2.5 times more bioactive mature product than do CHO cells expressing TGF-$\beta 1$ (Gentry et al., 1987, supra). Although the basis for these observations is presently unknown, the secondary structure of the chimeric TGF-$\beta 1/\beta 2$ precursor may significantly differ from the secondary structure of TGF-$\beta 1$, which secondary structure renders the chimeric TGF-$\beta 1/\beta 2$ subject to molecular processing events of a different intensity or nature. For example, the TGF-$\beta 1/\beta 2$ precursor may be a more favorable substrate for the factors involved in TGF-$\beta$ processing. Alternatively, the secondary structural characteristics of TGF-$\beta 1/\beta 2$ may allow it to interact with other processing factors or pathways not as accessible to TGF-$\beta 1$.

7. DEPOSIT OF MICROORGANISMS

The following transfectant has been deposited with the American Type Culture Collection, Rockville, Md., and has been assigned the listed accesion number.

| Transfectant | Plasmid | Accession No. |
|---|---|---|
| CHO-5β41, 2.5 CL 5 | p5β/dhfr | CRL 9959 |

The above-designated cell line has been deposited under the Budapest Treaty and will be irrevocably and without restriction or condition released to the public upon the issuance of patent on this application.

The present invention is not to be limited in scope by the cell line deposited or the embodiments disclosed herein which are intended as single illustrations of one aspect of the invention and any which are functionally equivalent are within the scope of the invention. Indeed, various modifications of the invention, in addition to those shown and described herein, will become apparent to those skilled in the art from the foregoing decription. Such modifications are intended to fall within the scope of the appended claims.

It is also to be understood that all base pair and amino acid residue numbers and sizes given for nucleotides and peptides are approximate and used for the purposes of description.

What is claimed is:

1. A chimeric transforming growth factor-$\beta 1/\beta 2$ comprising the amino acid sequence as depicted in FIG. 1 from amino acid number 279 to amino acid residue number 390.

2. An isolated DNA molecule encoding chimeric transforming growth factor-$\beta 1/\beta 2$ comprising the amino acid sequence as depicted in FIG. 1 from amino acid residue number 279 to amino acid residue number 390.

3. An isolated DNA molecule encoding chimeric transforming growth factor-$\beta 1/\beta 2$ comprising the amino acid sequence as depicted in FIG. 1 from amino acid residue number 1 to amino acid residue number 390.

4. A mammalian cell transformed with a DNA molecule coding for chimeric transforming growth factor-$\beta 1/\beta 2$ comprising the amino acid sequence as depicted in FIG. 1 from amino acid under 279 to amino acid number 390.

5. A mammalian cell transformed with a DNA molecule coding for chimeric transforming growth factor-$\beta 1/\beta 2$ comprising the amino acid sequence as depicted in FIG. 1 from amino acid number 1 to amino acid number 390.

6. A mammalian cell transformed with a DNA molecule coding for chimeric transforming growth factor-$\beta 1/\beta 2$ comprising the amino acid sequence as depicted in FIG. 1 from amino acid number 279 to amino acid number 390, wherein the coding region of said DNA molecule is under the control of a nucleotide sequence that regulates gene expression so that the cell produces chimeric transforming growth factor-$\beta 1/\beta 2$.

7. A mammalian cell transformed with a DNA molecule coding for chimeric transforming growth factor-$\beta 1/\beta 2$ comprising the amino acid sequence as depicted in FIG. 1 from amino acid number 1 to amino acid number 390, wherein the coding region of said DNA molecule is under the control of a nucleotide sequence that regulates gene expression so that the cell produces chimeric transforming growth factor-$\beta 1/\beta 2$.

8. The cell according to claim 6 or 7 which is a Chinese Hamster Ovary cell.

9. The cell according to claim 6 or 7 in which the nucleotide sequence that regulates gene expression comprises an SV40 promoter.

10. The cell according to claim 6 or 7 in which the nucleotide sequence that regulates gene expression comprises a promoter and a coding sequence for a selectable marker.

11. The cell according to claim 10 in which the selectable marker is dihydrofolate reductase.

12. A cell line designated CHO-5β41,2.5 CL5 as deposited with the American Type Culture Collection, having accession No. CRL 9959.

13. A method for producing chimeric transforming growth factor-$\beta 1/\beta 2$ comprising:
   (a) culturing a mammalian host cell transformed with a DNA molecule coding for chimeric transforming growth factor-$\beta 1/\beta 2$ comprising the amino acid sequence as depicted in FIG. 1 from amino acid number 279 to amino acid number 390, wherein the coding region of said DNA molecule is under the control of a nucleotide sequence that regulates gene expression so that a peptide or protein having chimeric transforming growth factor-$\beta 1/\beta 2$ activity is produced by the host cell; and
   (b) recovering the chimeric transforming growth factor-$\beta 1/\beta 2$ from the culture.

14. A method for producing chimeric transforming growth factor-$\beta 1/\beta 2$ comprising:
   (a) culturing a mammalian host cell transformed with a DNA molecule coding for chimeric transforming growth factor-$\beta 1/\beta 2$, comprising the amino acid sequence as depicted in FIG. 1 from amino acid number 1 to amino acid number 390, wherein the coding region of said DNA molecule is under the control of a nucleotide sequence that regulates gene expression so that a peptide or protein having chimeric transforming growth factor-$\beta 1/\beta 2$ activity is produced by the host cell; and
   (b) recovering the chimeric transforming growth factor-$\beta 1/\beta 2$ from the culture.

15. The method according to claim 13 or 14 in which the host cell is a Chinese Haster Ovary cell.

16. The method according to claim 13 or 14 in which the second nucleotide sequence which regulates gene expression comprises an SV40 promoter.

17. The method according to claim 13 or 14 in which the nucleotide sequence that regulates gene expression comprises a promoter and a coding sequence for a selectable marker for which the host cell is deficient, so that the host cell containing the chimeric transforming growth factor-$\beta 1/\beta 2$ coding sequence can be identified.

18. The method according to claim 17 in which the selectable marker is dihydrofolate reductase.

19. The method according to claim 18 further comprising exposing the host cell to methotrexate so that resistant colonies are selected which contain amplified levels of the coding sequence for dihydrofolate reductase and the chimeric transforming growth factor-$\beta 1/\beta 2$.

20. A method for producing chimeric transforming growth factor-$\beta 1/\beta 2$, comprising:
   (a) culturing transfectant CHO-5β41,2.5 CL5, deposited with the American Type Culture Collection and having accession No. CRL 9959;
   (b) recovering chimeric transforming growth factor-$\beta 1/\beta 2$ from the culture.

21. The method according to claim 20 in which the transfectant is cultured in the presence of methotrexate.

* * * * *